United States Patent [19]

Petrocelli

[11] Patent Number: 5,792,107

[45] Date of Patent: Aug. 11, 1998

[54] DISPOSABLE SAFETY SYRINGE

[76] Inventor: Pasqualino Petrocelli, Via Mameli, 41, I-10093 Collegno, Italy

[21] Appl. No.: 727,668

[22] PCT Filed: May 8, 1995

[86] PCT No.: PCT/EP95/01732

§ 371 Date: Dec. 2, 1996

§ 102(e) Date: Dec. 2, 1996

[87] PCT Pub. No.: WO95/30445

PCT Pub. Date: Nov. 16, 1995

[30] Foreign Application Priority Data

May 10, 1909 [IT] Italy .................... TO94 A 000376

[51] Int. Cl.[6] .................................................. A61M 5/00
[52] U.S. Cl. ................................... 604/110; 604/195
[58] Field of Search ............................ 604/110, 192, 604/195, 198, 263, 187, 218

[56] References Cited

U.S. PATENT DOCUMENTS

| | | | |
|---|---|---|---|
| 4,955,870 | 9/1990 | Ridderheim et al. | 604/195 |
| 5,114,410 | 5/1992 | Caralt-Batlle | 604/110 X |
| 5,180,369 | 1/1993 | Dysarz | 604/110 |
| 5,338,304 | 8/1994 | Adams | 604/110 |
| 5,487,732 | 1/1996 | Jeffrey | 604/195 X |

*Primary Examiner*—John D. Yasko
*Attorney, Agent, or Firm*—Keil & Weinkauf

[57] ABSTRACT

A disposable safety syringe in which the needle is automatically retracted after use to a position inside the tubular body of the syringe. The syringe, when retracted, cannot be reused; the needle-retraction means is not accessible to the operator, is not in contact with the substance to be injected, and at the end of the injection the needle is not axially advanced.

15 Claims, 7 Drawing Sheets

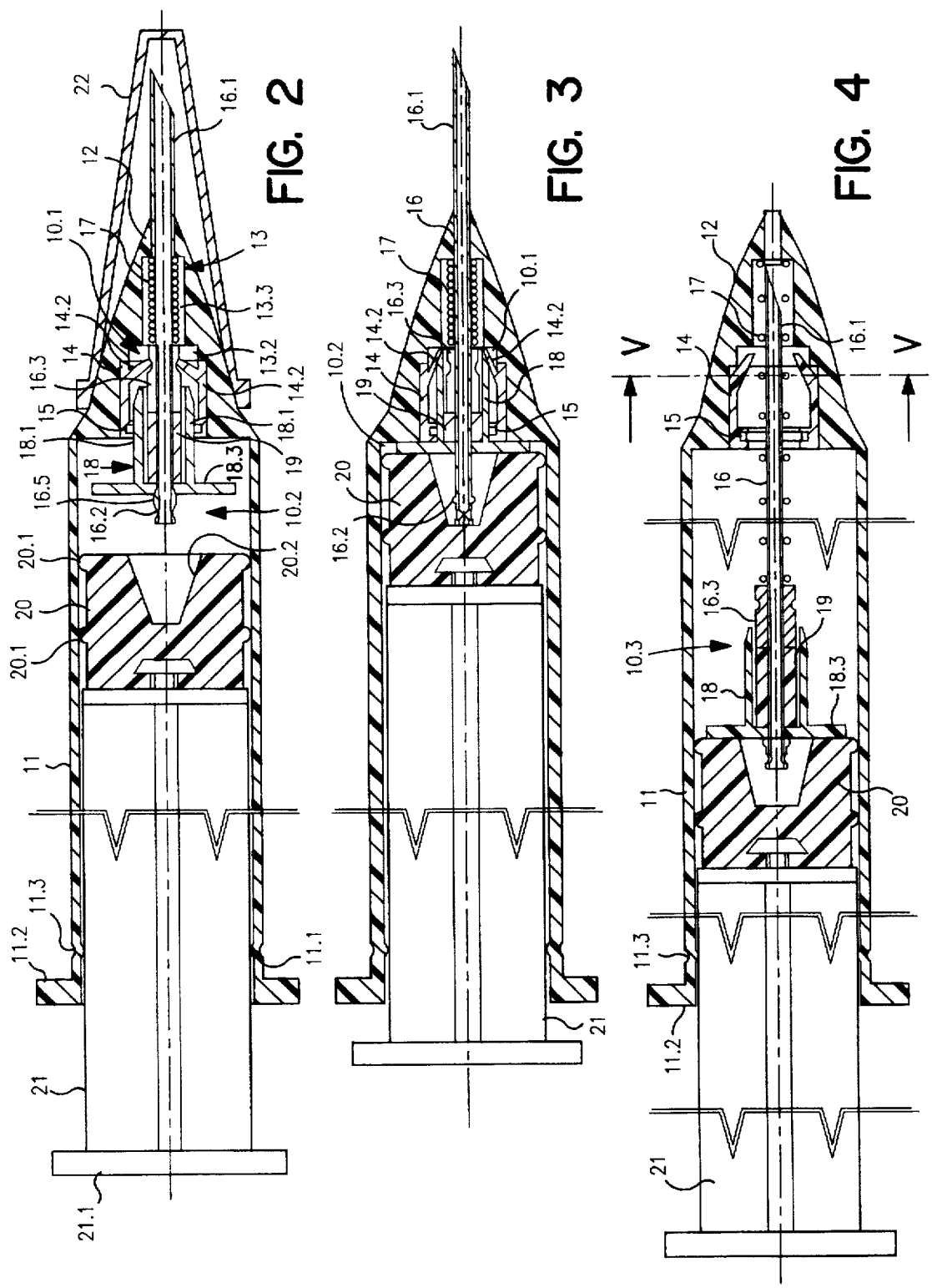

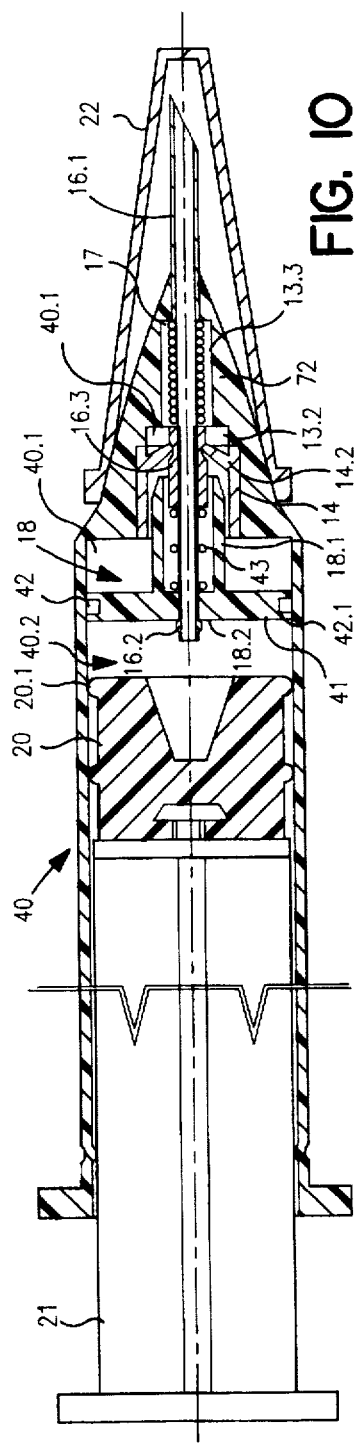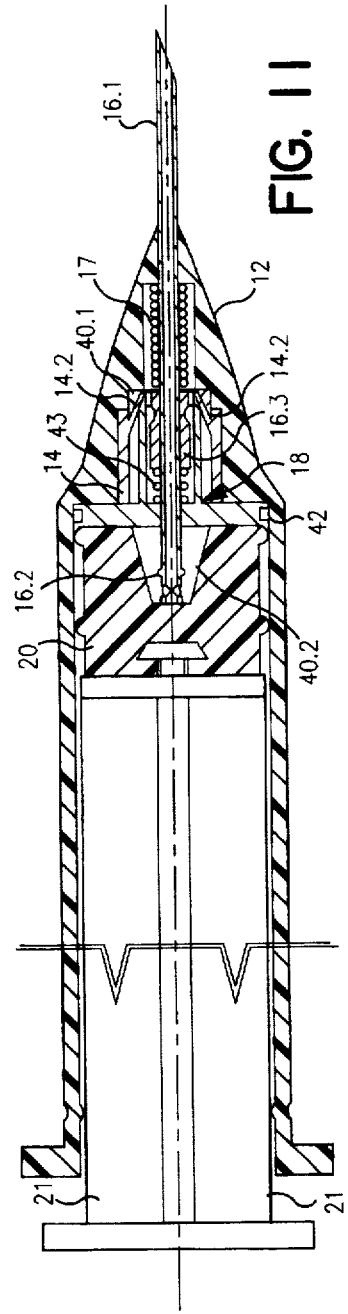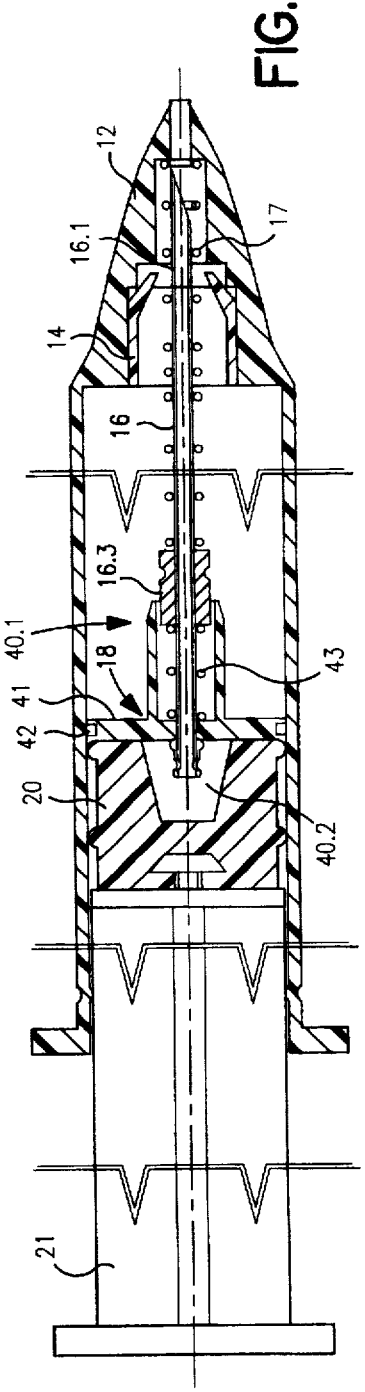

# 5,792,107

DISPOSABLE SAFETY SYRINGE

The present invention relates to a disposable safety syringe.

Disposable safety syringes in which the needle is automatically retracted into the tubular body of the syringe to a safe position after the injection are known.

However, such known disposable syringes have complex needle-retraction means. Moreover, these needle-retraction means are either positioned on the exterior of the syringe body (for example coaxially with the syringe plunger rod), and are therefore exposed to undesirable handling, or else, if positioned inside the syringe body, are in contact, during the injection, with the injection fluid, and as a result the latter can become contaminated.

In addition, in the known syringes of the type indicated, after the injection has been completed, the needle prior to its retraction—is advanced axially, presenting a possibly serious risk of injury to the patient, in order to disengage the needle from the means by which it is held in the active position. <<Please insert page 1a>>

The chief object of the present invention is therefore to provide a disposable safety syringe which will ensure that the needle is automatically retracted after the injection to a safe position inside the tubular body of the syringe, without allowing the syringe to be reused, and this by the use of structurally simple means that will operate safely and reliably.

Another object is to provide a disposable safety syringe as specified, in which the automatic needle-retraction means are not accessible to the operator and are never, at any point during the injection, in contact with the substance to be injected.

Yet another object is to provide a disposable safety syringe as stated, in which at the end of the injection the needle is not advanced axially, in order to guarantee the patient's safety.

Still another object is to provide a disposable safety syringe as indicated that is also suitable for use as a dispenser of a fluid, for example for mixing substances into powders or granules prior to injecting the latter. U.S. Pat. No. 5,114,410 discloses a disposable safety syringe which includes a tubular syringe body with a needle-supporting head through which a hollow needle passes and slides, a hollow piston which slides through the inside of the syringe body, and—before and during the injection—three non-communicating chambers, namely: a first chamber defined in the needle-supporting head and which contains retaining means that engage the needle so as to hold it in a fixed position—with tip extended from said head—in opposition to the action of return means; a second chamber defined in the tubular syringe body between said first chamber and said piston, and a third chamber inside the piston.

The first chamber and the second chamber are variable during the injection and separated by a discoid part, which is able to slide axially and leak tightly inside the front part of the syringe body.

The discoid part receives the head of the needle, which passes through it, and has fixed disengaging means to disengage said retaining means.

The discoid part and the needle as a whole are pushed forward by the piston and the volume of the first chamber reduces, when the piston completes its operative run.

At this stage, the discoid part, and the needle with it, move slightly forward as they are pushed by the piston and the disengaging means disengage the retaining means from the needle, thereby releasing the needle, which is suddenly introduced into the piston's cavity (i.e. the third chamber) through the action of the return means.

In other words, as the piston completes its operative run, it before pushes forward the needle and immediately after springs a mechanism which automatically and suddenly introduces the needle into the axial cavity inside the piston.

However, during the completion of the piston operative run, the injection has not yet been completed and the needle axially advanced—prior to its retraction—presents a serious risk of injury to the patient (e. g. a vein could be pierced).

Furthermore, since no control or braking means are provided to control and/or braking the needle when suddenly retracted into the third chamber (i.e. the axial cavity of the piston), another serious risk of injury to the patient occurs (e. g. a vein could be rent if the needle is snatched off).

In consideration of these objects, the present invention provides a disposable safety syringe, the essential feature of which is the subject matter of the main claim, which should be regarded as incorporated here in its entirety.

Other advantageous features are indicated in the subordinate claims, which should also be regarded as incorporated here in their entirety.

The present invention is described in detail hereinafter, with reference to the attached drawings which are provided purely by way of non-restricting example and in which:

FIG. 2 is a view in axial section, on a larger scale and partly interrupted, of the disposable safety syringe shown in FIG. 1;

FIGS. 3 and 4 are views similar to FIG. 2 but show the syringe according to the invention at the conclusion of the injection, and with the needle automatically retracted into the tubular syringe body in the safety position, respectively; in these views the cap is removed;

FIGS. 10 to 12 are views similar to those of FIGS. 2 to 4 respectively, but show another illustrative embodiment of the invention;

Figure 1:
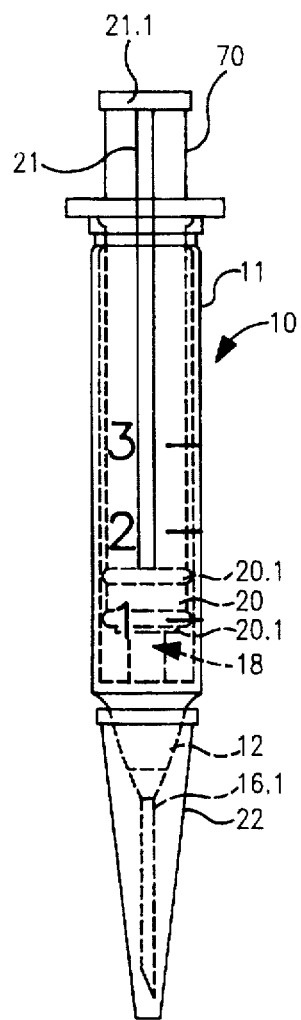
FIG. 1 is an elevation of the disposable safety syringe in a first illustrative embodiment of the invention, as presented for use and provided with a cap to protect the needle projecting from the syringe.

First illustrative embodiment of the invention (FIGS. 1–7).

With reference initially to FIGS. 1 to 7 of the drawings, the numeral 10 (FIG. 1) indicates the whole of the disposable safety syringe in a first illustrative embodiment of the present invention.

The syringe 10 comprises a generally tubular cylindrical syringe body 11, which may be made of a transparent plastic material, with an integral conical needle-supporting head 12 coaxial with the syringe body 11.

This conical head 12 is perforated by an axial through hole 13 (FIG. 6) forming four intercommunicating cylindrical axial cavities 13.1–13.4, whose diameters decrease towards the conical tip of the head.

More specifically, in said hole 13 a first cylindrical axial cavity 13.1 of greatest diameter is open towards the inner space of the syringe body 11. Following this first cavity 13.1 come a second and a third cylindrical axial cavities 13.2, 13.3, their diameters decreasing in that order, and finally into a fourth cylindrical axial cavity 13.4 of least diameter and open to the exterior at the conical tip of the head 12. Between the third and fourth cavities 13.3, 13.4 is a shoulder 13.5.

Force-fitted in the first axial cavity 13.1 of the hole 13 is a coaxial bush 14, which may be made of a plastic material and comprises, towards the inner space of the syringe body 11, an internal circumferential groove 14.1 into which a sealing ring 15, which may be of rubber, is inserted. In addition, two diametrically opposite integral retaining fingers 14.2 (FIG. 5) project symmetrically from said bush 14 into the interior of the bush so as to converge towards each other towards the conical tip of the head 12. The free ends of these fingers 14.2 stop short of each other. In said fourth axial cavity 13.4 of the hole 13 is an axially movable hollow syringe needle means 16. This may be a long steel needle with a hole down its axis whose tip 16.1 extends externally from the head 12, while its opposite end 16.2 extends into the inner space of the syringe body 11 after passing axially through said bush 14.

Fitted at an intermediate point to this needle 16 is a coaxial needle-supporting sleeve 16.3 around which runs an external circumferential groove 16.4 in which the free ends of the retaining fingers 14.2 of the bush 14 are normally engaged.

A helical compression spring 17 placed coaxially around the needle 16 is installed between the end of the needle-supporting sleeve 16.3 nearest the shoulder 13.5 and the shoulder 13.5 itself, in such a way as to be fully compressed. Said needle means 16 is thus normally held in a fixed position relative to the needle-supporting head 12 by means of said retaining fingers 14.2, which resist the elastic force of the spring 17 on the needle-supporting sleeve 16.3 that would cause the needle means 16 to retract axially into the tubular syringe body 11.

A parting member 18 slides axially and leak tightly on the end portion, near the end 16.2, of the needle means 16.

This parting member 18 comprises a cylindrically-walled cup body 18.1, which may be made of a plastic material, whose base 18.2 contains an axial hole for its coaxial mounting, and axial and leak tight sliding, on the needle means 16, and whose cylindrical wall slides inside and is guided within the bush 14 in leak tight contact with the annular seal 15. The base portion 18.2 of this cup body 18.1 extends into the inner space of the tubular syringe body 11, while its open axial end portion which has a tapering wall points from behind towards the retaining fingers 14.2.

An elastic tubular sheath 19, which may be of rubber, is fitted coaxially on said end portion, close to the end 16.2, of the needle means 16, and is interposed, to act as a return spring, between the needle-supporting sleeve 16.3 and the base 18.2 of the cup body 18.1. The tubular wall of this cup body 18.1 coaxially surrounds the sheath 19 but allows it to deform elastically. In this way the cup body 18.1 is normally held with its open axial end portion at a distance from the retaining fingers 14.2 as they sit in the groove 16.4 around the needle-supporting sleeve 16.3 (see FIG. 6).

Also an integral flange 18.3 that stops radially short of the inner cylindrical surface of the syringe body 11 extends radially from the base 18.2 of said cup body 18.1.

The cup body 18.1 is prevented from sliding axially along the free end 16.2 of the needle means 16 by an external annular swelling 16.5 of the needle means 16, beyond which free end 16.2 it extends into the inner space of the tubular syringe body 11. It will be observed that this free end 16.2 of the needle means has not only an axial opening but also a plurality of radial openings communicating with the inner space of the tubular syringe body 11 in order to facilitate the passage of the fluid.

A plurality of through holes 18.4 whose axes converge towards each other in the direction of this end 16.2 of the needle means 16 are also provided in said flange 18.3 on the cup body 18.1 and lead, on one face of this flange, from close to the radial openings of the needle means and, on the opposite face, towards the bush 14.

Housed inside tubular syringe body 11 in such a way as to be able to slide axially and leak tightly within it is a plunger 20 (FIGS. 2–4) having a generally cylindrical body of, for example, rubber, and having two annular beads 20.1 to act as a seal against the cylindrical tubular wall of the syringe body 11.

This plunger 20 is moved axially inside said tubular syringe body 11, between an axially forward position close to the head 12 and an axially retracted position away from this head 12, by means of an axial rod 21 connected to said plunger.

On the front end of this plunger 20, that is opposite the end 16.2 of the needle means 16, is a frustoconical axial cavity 20.2 into which this end 16.2 of the needle means 16 passes when the plunger 20 comes into contact with the flange 18.3 of the cup body 18.1.

This rod 21 has an axial end remote from the plunger 20 that extends beyond the axial end 11.1 of the tubular syringe body 11 furthest from the head 12. Mounted on this axial end is an actuating disc 21.1.

A flange 11.2 is formed integrally at this axial end 11.1 of the syringe body 11 to enable the body 11 of the syringe 10 to be grasped.

Also an internal annular bead 11.3 is formed in the cylindrical wall of the syringe body 11, at this axial end 11.1, as a means of guiding the rod 21 in its axial movements and of preventing the plunger 20 from being axially withdrawn, owing to interference with its annular beads 20.1.

The above arrangement means that the syringe 10, before and during the injection, contains two non-communicating chambers 10.1 and 10.2, as follows:

a first chamber 10.1 defined between the axially hollow head 12 and the parting member 18 and including the axial cavities 13.2, 13.3, the inner space of the bush 14 and the inner space of the cup body 18.1 that slides leak tightly in said bush; through which first chamber said needle means 16 passes; and a leak tight second chamber 10.2 defined within the tubular syringe body 11 between said head 12, said bush 14 and said cup body 18.1 on the one hand, and the piston 20 on the other; the free end 16.2 of the needle means 16 passes axially into this second chamber.

The volumes of these chambers 10.1, 10.2 of the syringe 10 can be varied down to a minimum volume that occurs at the end of the injection (FIG. 3), as will be seen more particularly below.

OPERATING THE SYRINGE 10

The syringe 10 is presented for use as illustrated in FIGS. 1 and 2, that is to say bearing a cap 22 to protect the tip 16.1 of the needle means 16. The plunger 20 is positioned level with, for example, the "1" mark on a graduated scale indicating the capacity, for example in c.c., of the tubular syringe body 11.

With the cap 22 removed and the fluid to be drawn in prepared, the latter is drawn in by pulling by hand on the rod 21 to withdraw said plunger 20 in the axial direction. In this way the indrawn fluid passes along the needle means 16 into said second leak tight chamber 10.2. When drawing-in has been completed the plunger 20 is moved axially forward in order to purge, from the second chamber 10.2 through the needle means 16, at least a substantial part of the air still contained in the syringe body 11. After purging, the exact amount of liquid contained in the second chamber 10.2 of the syringe 10 is read off on the graduated scale.

If, before the injection is carried out, it is necessary to use the measured fluid contained in the second chamber 10.2 to dissolve powdered or granular substances for injection, the plunger 20 is advanced axially still further until in contact with the flange 18.3 of the cup body 18.1.

The correct approach of the plunger 20 to the cup body 18.1 is facilitated by the presence of the elastic tubular sheath 19 which, while allowing the cup body 18.1 to advance axially towards the conical tip of the head 12, exerts a backward force which increases the axial effort required of the operator. It is in fact best at this point for the flange part 18.3 of the cup body 18.1 not to contact the bush 14, i.e. it is best that the first and second chambers 10.1, 10.2 of the syringe 10 should not be reduced to their smallest volumes, for reasons which will be made clear later. The elastic braking action applied by this sheath 19 alerts the operator not to continue with the axial advance of the plunger 20.

After mixing the fluid and powder or granules, the operator repeats the operations of drawing them in and purging the air as described above.

He then carries out the injection in the conventional manner reducing to their minimum volumes both the second chamber 10.2, from which the injectable substance is expelled, and the first chamber 10.1 of the syringe 10 by axially advancing, initially, the plunger 20 into contact with the flange 18.3 of the cup body 18.1, and then also the cup body 18.1 until its flange 18.3 is in contact with the bush 14 and the base of the head 12 of the syringe body 11 (FIG. 3). The injected substance passes out of the second chamber 10.2 through the needle means 16 without entering the first chamber 10.1.

It will be observed that the holes 18.4 in the flange part 18.3 of the cup body 18.1 allow the injection fluid to flow back from the inner space of the tubular syringe body 11 into the axial cavity 20.2 of the plunger 20 and from this into the admission apertures in the needle means 16, when the end 16.2 of the needle means is received inside said cavity and the plunger 20 is pressed against the flange 18.3.

As will have been seen from the above, reducing the two chambers 10.1, 10.2 to their minimum volume has the effect of expelling from the second chamber 10.2 the entire useful quantity of injection fluid through the needle means 16 and simultaneously disengaging the retaining fingers 14.2 from the needle support 16.3—and hence from the needle means 16—in the first chamber 10.1. What happens is that in the first chamber 10.1, the parting member 18, which is advanced axially by the plunger 20, engages and pushes apart, by means of the open front axial end of its cup body 18.1, in this position, the free ends of the retaining fingers 14.2 of the bush 14, thereby freeing the needle-supporting sleeve 16.3. This pushing apart of the retaining fingers 14.2 is permanent.

(It will be noticed that the needle means 16 remains fixed and immovable relative to the head 12 until the two chambers 10.1, 10.2 have been reduced to their minimum volume).

Therefore, as the operator releases his hand pressure on the rod 21 and on the plunger 20, the spring 17 becomes free to exert its elastic retaining action on the needle means 16. This elastic retaining action is also exerted through the needle support 16.3 and the elastic sheath 19—which cooperates elastically—on the parting member 18 and, via the latter, on the plunger 20. The consequence is that the needle means 16, parting member 18 and plunger 20 are automatically retracted axially into the tubular cavity of the syringe body 11 at least sufficiently to completely retract the needle means 16 with its tip 16.1 into the head 12. In this retraction, the cup body 18.1 comes away from the bush 14.

In this condition the syringe 10 contains a single common chamber 10.3 (FIG. 4), inside which are the plunger 20;. the parting member 18, the elastic sheath 19 and the needle means 16, all kept retracted back from the conical tip of the head 12 by the elastic returning action of the spring 17.

The syringe 10 is thus automatically placed in the safety condition with the needle means disarmed and no longer usable.

Figure 8:
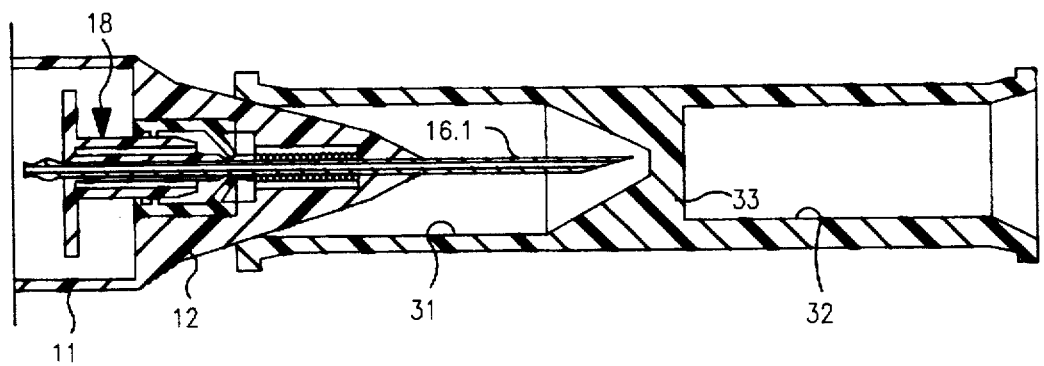
FIGS. 8 and 9 are views similar to FIG. 6, but on a different scale, and illustrating an alternative cap positioned in the first case as a protection of the needle projecting from the syringe and in the second case as a funnel dispenser of fluid into the needle.
Figure 9:
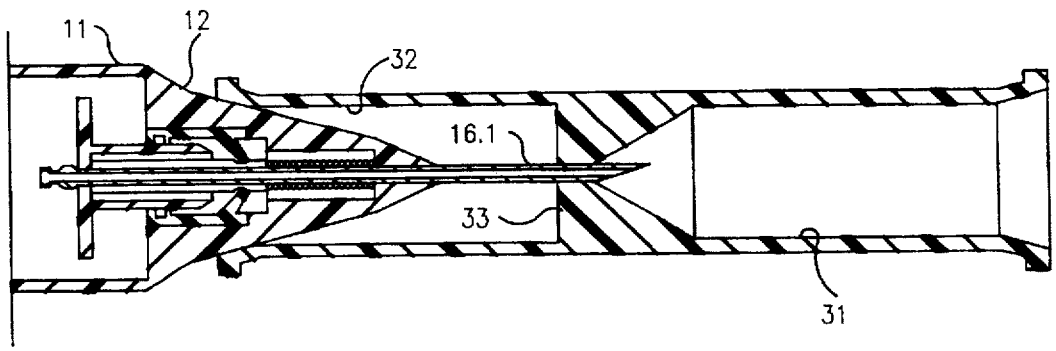
Figure 13:
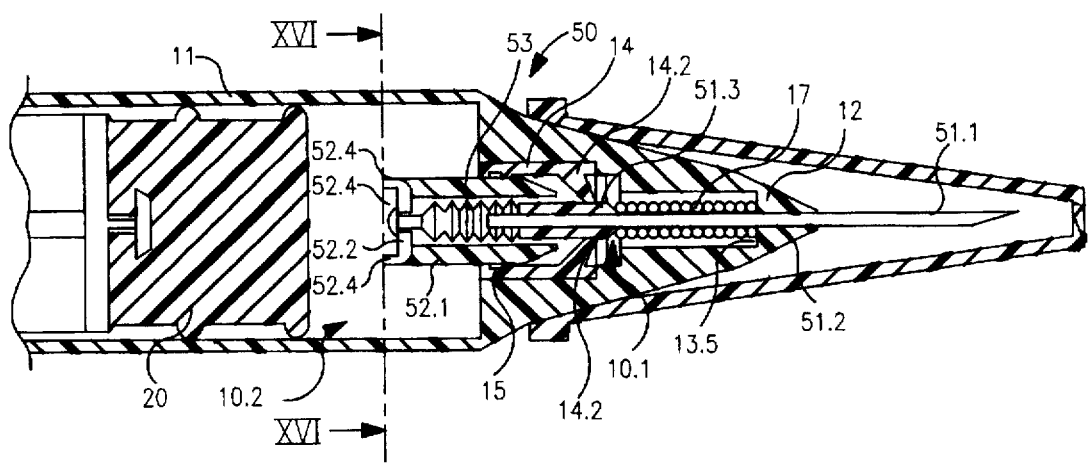
FIGS. 13 to 15 are also views similar to those in FIGS. 2 to 4, but show yet another illustrative embodiment of the invention.
Figure 14:
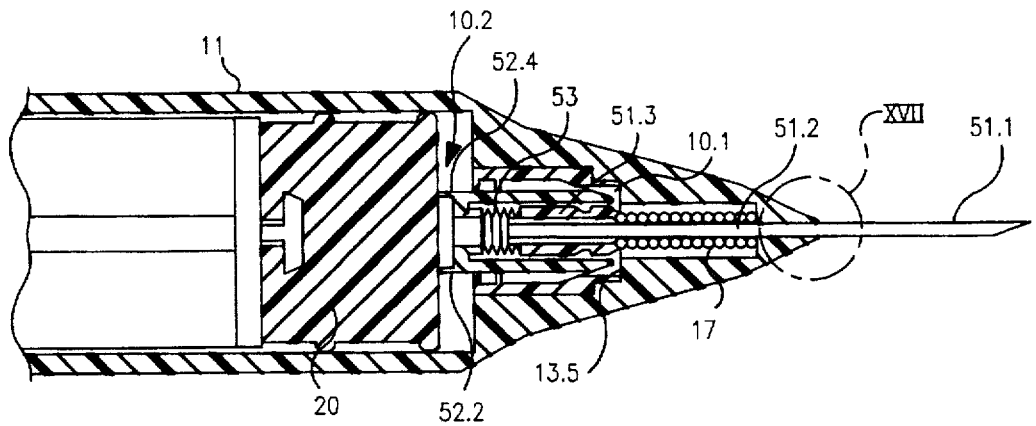
Figure 15:
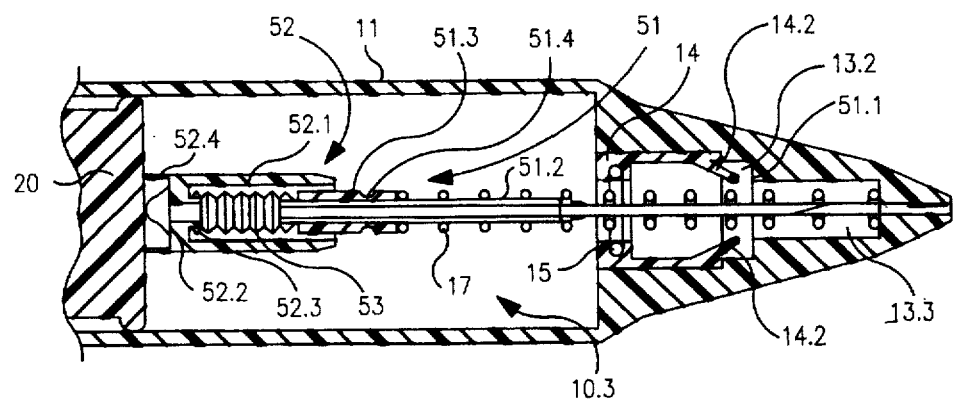

Alternative embodiment depicted in FIGS. 8 and 9.

This embodiment comprises a cap marked 30 and made, for example, of a relatively soft plastic material, which cap comprises two axial cavities 31 and 32 separated from each other by an intermediate septum 33. The inner end of the axial cavity 31 is conical.

By this arrangement, said cap 30 can assume two different positions on the head 12 of the syringe 10. In the first position, the cap 30 protects the needle means 16 (FIG. 8), which sits inside its cavity 31 in the conventional way. In the other position, rotated 180° with respect to the first position, the tip 16.1 of the needle means 16 is pushed through the septum 33 of the cap 30 and the cavity 31 of the cap, into which the tip projects, can be used as a funnel to facilitate the drawing-in of the fluids to be injected or mixed (FIG. 9).

Second illustrative embodiment of the invention (FIGS. 10–12).

The disposable safety syringe in this embodiment is denoted by the general reference 40 (FIG. 10) and is in most respects similar to the syringe 10 of the first embodiment described earlier.

In the following description, those parts of syringe 40 which are similar to those of syringe 10 are marked with the same reference numerals.

By way of an alternative, in the syringe 40 the cup body 18.1 of the parting member 18 comprises an integral flange 41 that extends radially from its base portion 18.2 into virtual contact with, or else very close to, the wall of the tubular syringe body 11. A sealing ring 42, which may be of rubber and is housed in a corresponding external circumferential groove 42.1, acts as a seal between this flange and said wall, so that the syringe 40 contains—before and during the injection—two non-communicating chambers 40.1 and 40.2 (FIG. 10), as follows:

- a first chamber 40.1, defined between the cup body 18.1 with flange 41, part of the wall of the tubular syringe body 11 and the axially hollow head 12; through which first chamber 40.1 the needle means 16 passes axially; and
- a fluid-leaktight second chamber 40.2 defined, in the tubular syringe body 11, between said cup body 18.1 with flange 41 and the plunger 20.

It will be observed that the cup body 18.1 in the syringe 40 is guided leak tightly along the walls of the tubular syringe body 11 rather than, as in syringe 10, within the bush 14. The tubular wall of the cup body 18.1 of the syringe 40 enters this bush 14 coaxially with radial play.

Also, instead of the elastic sheath 19 of the syringe 10, the syringe 40 comprises, in the same arrangement and with the same function, a helical return spring 43.

For the remainder, the description of the syringe 10 should be referred to.

As the above will have made clear, the volumes of said two chambers 40.1 and 40.2 of the syringe 40 can be varied down to a condition of minimum volume, which occurs at the end of the injection (FIG. 11), as in the case of the syringe 10, the description of which should be referred to for the operation of the syringe 40 as well.

After use, the volume of the first chamber 40.1 of the syringe 40 is much enlarged (FIG. 12) and contains the needle means 16 and parting member 18 automatically retracted axially into said tubular body 11 with the plunger 20 by the elastic return means 17, at least sufficiently for complete retraction of the needle means 16 and its tip 16.1 inside the head 12. The second chamber 40.2 is kept at the minimum volume. This is the safety condition of the syringe 40, which can now no longer be used.

Third illustrative embodiment of the invention (FIGS. 13 to 18)

The disposable safety syringe in this embodiment is denoted by the general reference 50 (FIG. 13) and it too is very largely similar to syringe 10.

In the following description also, those parts of the syringe 50 which are similar to those of syringe 10 are indicated by the same reference numerals.

Figure 17:
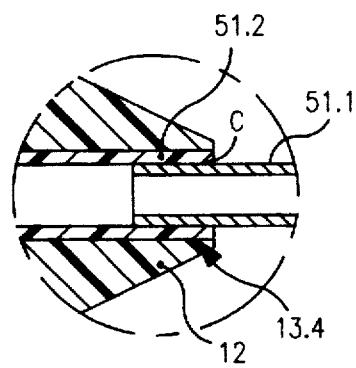
FIG. 17 is a detail view, on a larger scale, of the area marked XVII in FIG. 14.
Figure 6:
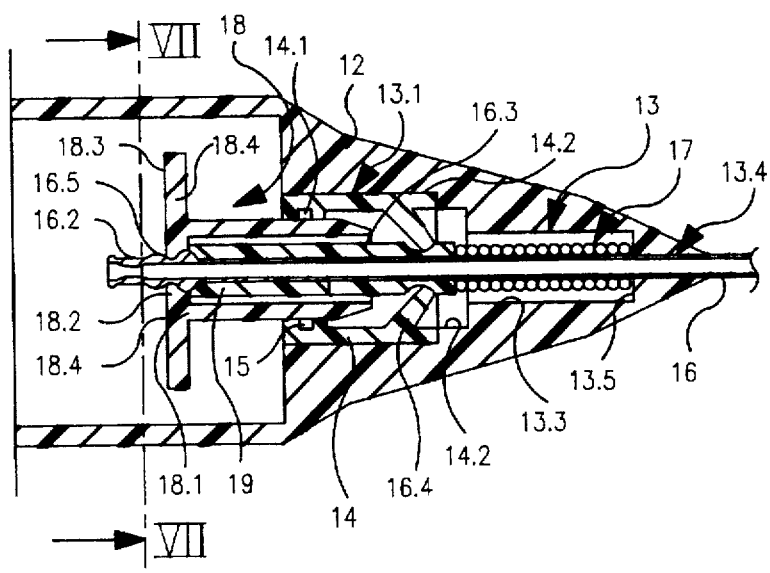
FIG. 6 is a detail view, on a larger scale, of the area marked VI in FIG. 2.

As an alternative, the syringe 50 contains in the first place a composite hollow needle means 51. This needle means 51 comprises a short conventional hollow steel syringe needle 51.1. The needle 51.1 is inserted coaxially and mounted in fluid communication at one end of an axial needle-supporting cannula 51.2, which may be made of a plastic material. The tip of the needle 51.1 normally projects from the conical end of the needle-supporting head 12, through the axial hole 13.4, relative to which it can slide freely axially with the needle-supporting cannula 51.2. It can be fixed to the cannula 51.2 by, for example, an adhesive C (FIG. 17).

Fixed to this cannula 51.2 in an intermediate position is a coaxial needle-supporting sleeve 51.3, which has one axial end towards the shoulder 13.5. This sleeve 51.3 has an external circumferential groove 51.4 in which the free ends of the retaining fingers 14.2 of the bush 14 are normally engaged.

A helical compression spring 17 is mounted coaxially on the cannula 51.2 and is interposed between the end of the needle-supporting sleeve 51.3 nearest the shoulder 13.5 and this shoulder 13.5 itself, in such as way as to be fully compressed.

Said needle means 51 is thus stably held in a fixed position relative to the needle-supporting head 12, in the same way as the needle means 16 in the first embodiment.

As another alternative, a parting member 52 is provided, comprising a cylindrically-walled cup body 52.1 which may be made of a plastic material. The base 52.2 of this cup body has an axial hole and is provided with a short tubular bead 52.3 coaxial with the hole itself and extending inwards.

The cylindrical wall of this cup body 52.1 is slid into and guided by the bush 14 in leaktight contact with the sealing ring 15.

The base portion 52.2 of this cup body 52.1 extends into the inner space of the tubular syringe body 11, while its opposite axial end, the wall of which is tapered, points towards the retaining fingers 14.2.

In addition, from the base 52.2 of the cup body 52.1 a plurality of teeth 52.4, distributed and distanced from each other around the circumference in the form of a crown, project towards the inner space of the syringe body 11 and point towards the plunger 20.

Replacing the tubular elastic sheath of the syringe 10 is an elastic sleeve 53 of bellows construction. This elastic sleeve 53 is fitted leak tightly at one end over the axial tubular bead 52.3 of the cup body base 52.1, and at the other end over the free axial end of the needle-supporting cannula 51.2. This provides an axial fluid-leaktight passage between the inner space of the tubular syringe body 11 and the hollow needle 51.1.

It will be observed that in this embodiment the plunger 20 is of conventional design.

In this way the syringe 50 is likewise provided before and during the injection—with two non-communicating chambers, as follows:

- a first chamber 10.1 defined between the axially hollowed head 12 and the parting member 52 and including the axial cavities 13.2, 13.3, the inner space of the bush 14 and the inner space of the cup body 52.1; the needle means 51 (cannula 51.2) and the elastic sleeve 53 pass through this first chamber 10.1; and
- a fluid-leaktight second chamber 10.2 (equivalent to the same chamber in syringe 10).

OPERATION

Drawing the fluid into the syringe 50 and measuring it are performed as in the syringe 10, though it will be noted that the function of the elastic sheath 19 of said syringe 10 is here performed by the elastic bellows sleeve 53, which can deform in the axial direction.

The injection is then performed in an entirely conventional manner by reducing the volume of the chamber 10.2, from which the fluid is expelled at pressure by the plunger 20 through the fluid-leaktight passage defined by the axial hole in the base 52.2 of the cup body 52.1, by the elastic sleeve 53, by the needle-supporting cannula 51.2 and by the hollow needle 51.1.

During this operation the plunger 20 presses against the toothed crown 52.4 of the cup body 52.1 and, while the plunger is pushing the parting member 52 axially towards the conical end of the head 12, the fluid passes through these teeth and enters the axial hole in the base 52.2. The injection fluid does not enter the chamber 10.1. The elastic bellows sleeve 53 is compressed elastically.

The conically tapering front end of the cup body 52 pushes apart the retaining fingers 14.2, while the volume of the two chambers 10.1 and 10.2 reduces to the minimum. (The needle means 51 remains fixed and immobile relative to the head 12 until the chambers 10.1, 10.2 have been reduced to their minimum volume.) This frees the needle-supporting sleeve 51.3 and the spring 17 can exert, in cooperation with the elastic sleeve 53, its elastic returning action, which will fully retract the needle means 51 into the safe position inside the syringe body 11, while the cup body 52 disengages from the bush 14 and retreats in the same way into said inner space with the needle means.

The result is a single common chamber 10.3 inside the syringe 50, containing the plunger 20, the parting member 52 and the needle means 51 with elastic sleeve 53. The tip of the needle 51.1. is retracted into this chamber 10.3 in the safe position.

The main advantage of this embodiment is its structural simplicity and the fact that it uses a conventional hollow needle 51.1 and conventional plunger 20.

As an alternative to what has been described and illustrated, the needle means may be constructed as a single plastic part including the hollow needle part proper, the cannula part and the needle-supporting sleeve.

Furthermore the elastic sleeve, which connects said needle means with the axially perforated base of the cup body, can be replaced by a telescopic tubular structure cooperating with an elastic return means, such as a coaxial helical compression spring.

Figure 20:
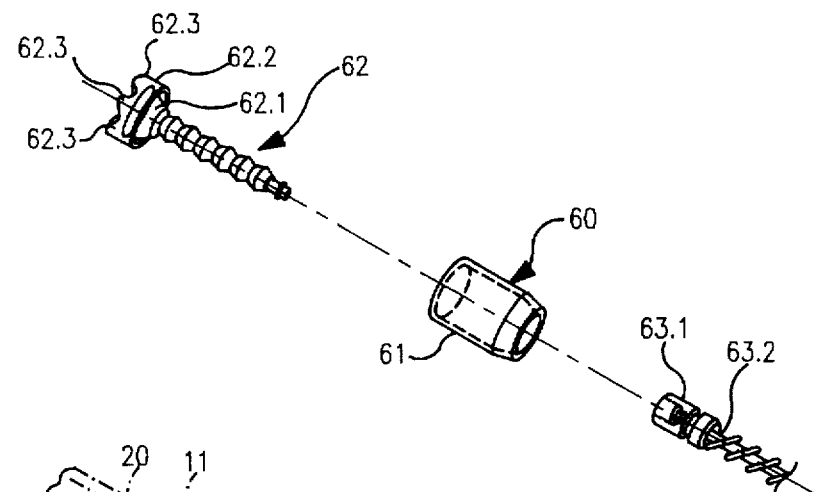
FIG. 20 is a view similar to FIG. 19, but with parts still further broken up and the needle interrupted for the sake of clarity of the drawing (the syringe body and the plunger have been omitted)
Figure 19:
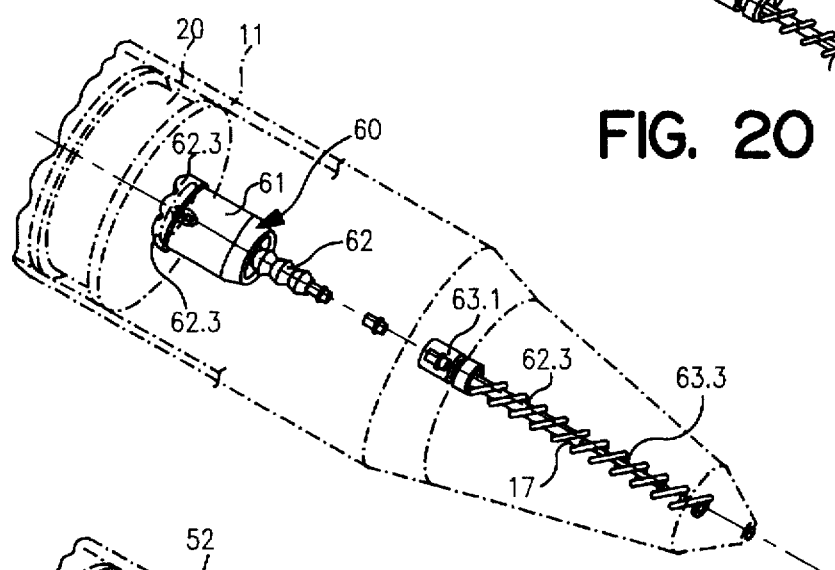
FIG. 19 is a view similar to FIG. 18, but shows an alternative embodiment.
Figure 18:
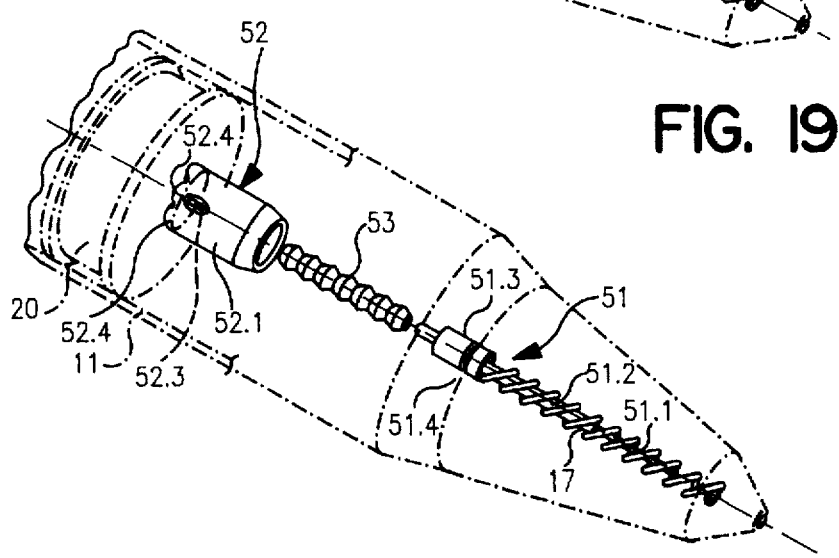
FIG. 18 is an exploded, partial perspective view of the syringe shown in FIGS. 13 to 15, in which the syringe body and the plunger are shown schematically in chain lines.

Alternative embodiment as shown in FIGS. 19 and 20.

This alternative employs a simplified parting member 60 consisting of a simple cylindrical tubular body 61, which may be made of plastic material, whose axial end nearest the retaining fingers 14.2 is conically tapered. This tubular body 61 is slid into and guided axially within the bush 14 in leaktight contact with the sealing ring 15, in the same way as the cup body 52.1 described earlier.

An elastic sleeve 62 of bellows-type construction, which may be of an elastomeric material, is inserted coaxially and is connected to said tubular body 61 at its axial end 62.1, which is flared like a funnel. This funnel end 62.1 has a circumferential lip 62.2 on the outer edge of the body 61 remote from the retaining fingers 14.2. The funnel end 62.1 of the elastic sleeve 62 is thus open in the inner space of the syringe body 11. On this lip 62.2 is an arrangement of integral teeth 62.3 resembling a crown projecting towards the plunger 20. At its other axial end said elastic sleeve 62 is connected in a leaktight manner to a needle-supporting sleeve 63.1, which is in fluid communication with, and integral with, an axial end of an axial needle-supporting cannula 63.2. Said cannula 63.2 is connected leak tightly, at its other axial end, to a hollow syringe needle 63.3, which may be made of steel.

For other aspects see the description referring to FIGS. 13 to 18.

Figure 21:
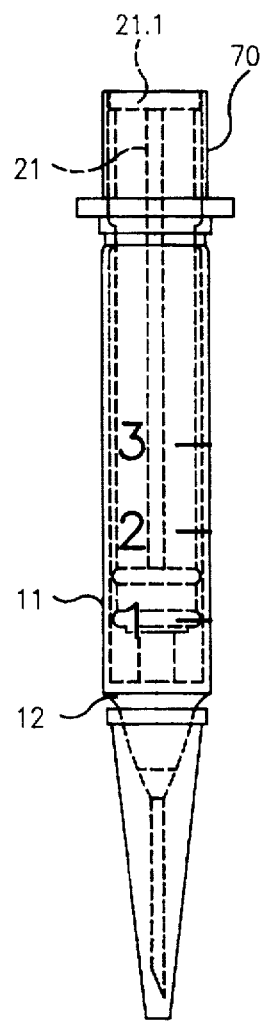
FIG. 21 is a view similar to FIG. 1, but shows another alternative embodiment.
Figure 22:
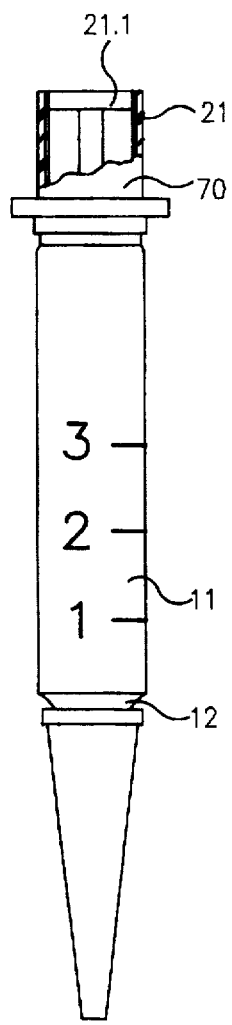
FIG. 22 is similar to FIG. 21, but with part in section.
Figure 5:
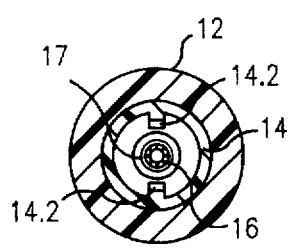
FIG. 5 is a sectional view taken on the line V—V marked in FIG. 4.
Figure 7:
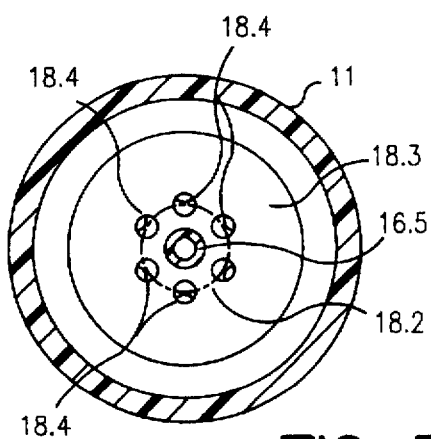
FIG. 7 is a sectional view on the line VII—VII marked in FIG. 6.
Figure 16:
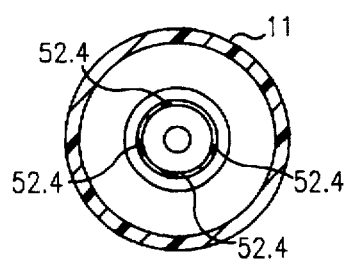
FIG. 16 is a sectional view on the line XVI—XVI marked in FIG. 13.

Alternative as shown in FIGS. 21 and 22.

In this alternative the syringe body 11 comprises, at its axial end remote from the head 12, an axial, integral, generally cylindrical jacket 70 which encircles the rod 21 and into which the actuating disc 21.1 of this rod 21 passes at the end of the injection stroke.

This arrangement makes it more difficult to prevent the automatic disarming of the syringe at the end of the injection stroke of the plunger 20.

I claim:

1. Disposable safety syringe which includes a generally tubular syringe body (11) with a needle-supporting head (12) through which passes a through hole (13), in which a hollow needle means for a syringe (16, 16.3; 51; 63.1, 63.2, 63.3) is able to slide axially so as to be extended and retracted relative to this head, and a plunger (20) that is moved axially and leaktightly inside said syringe body (11) by a rod (21), between an advanced position close to the head (12) and a retracted position remote from this head, and vice versa, and in which said syringe (10, 40, 50)—before and during the injection—comprises, between the body (11), the head (12) and the plunger (20), two non-communicating chambers, namely a first chamber (10.1, 40.1), defined in or beginning at said head (12) and through which said needle means passes and which contains retaining means (14.2) that engage the needle means so as to hold it in a fixed position—with tip (16.1) extended from said head (12)—in opposition to the action of return means (17) tending to retract this needle means inside said tubular syringe body (11), and a fluid-leaktight second chamber (10.2, 40.2) defined in said tubular syringe body (11) between said first chamber (10.1, 40.1) and said plunger (20) and with which said needle means communicates leaktightly, and which also includes disengaging means (18, 52, 60) provided so as to slide leaktightly relative to said two chambers (10.1, 10.2, 40.1, 40.2) between a rest position, in which they are situated when said plunger (20) is in a retracted position, and a working position, in which they permanently disengage said retaining means (14.2) from said needle means when said plunger (20) is moved into this advanced position at the bottom of its stroke, characterized in that said disengaging means (18, 52, 60) are provided so as to slide relative to said needle means (16, 16.3; 51; 63.1, 63.2, 63.3) and said two chambers (10.1, 10.2, 40.1, 40.2) are variable during the injection, namely the volume of the first chamber (10.1, 40.1) reduces when said disengaging means are moved towards their working position, while said needle means remains stationary and the volume of the second chamber (10.2, 40.2) reduces as said plunger (20) is moved towards its advanced position, in such a way that when said disengaging means (18, 52, 60) are in the rest position, an injection substance is drawn in said second chamber (10.2, 40.2) through said needle means (16, 16.3; 51; 63.1, 63.2, 63.3) by manually withdrawing said plunger (20) in the axial direction, and is then injected, by a reverse movement of this plunger, without entering said first chamber (10.1, 40.1), while at the end of the injection said plunger (20) is moved into said advanced position at the bottom of its stroke and said disengaging means (18, 52, 60) adopt their working position, and in that, in this condition, in the interior of said tubular syringe body (11) a single common chamber (10.3) is provided, in which said return means (17) automatically cause this needle means to retract, together with said plunger (20), as the manual pressure applied by the operator on the plunger (20) is released—without any preliminary advancing of the needle means relative to said head (12)—such that the tip (16.1) of the needle means is retracted relative to the head (12), thereby disarming the syringe (10) and making it no longer usable.

2. Syringe according to claim 1, characterized in that said needle means (16, 16.3)—before and during the injection—have an end (16.2) projecting into said second chamber (10.2), in that said disengaging means (18) comprise a cup body (18.1) having generally cylindrical tubular walls and an axially perforated base and being mounted so as to slide axially and leak tightly relative to said needle means (16, 16.3) of which body an open axial end portion extends towards said retaining means (14.2), in that said retaining means (14.2) comprise engaging members, for example fixed retaining fingers, which—before and during the injection—engage said needle means (16, 16.3) and oppose the action of said return means (17) for retracting the needle, and in that—before and during the injection—said cup body is inserted so as to slide leaktightly (seal 15) with its tubular wall in a corresponding aperture (bush 14) in said first chamber (10.1), while the base portion (18.2, 18.3) of this cup body extends into said second chamber (10.2) in opposition to said plunger (20), in such a way that, at the conclusion of the injection, said cup body is pushed by the plunger and disengages said retaining means from said needle means by means of its end portion and is then retracted with said needle means inside the tubular syringe body.

3. Disposable syringe according to claim 1, characterized in that one end (16.2) of said needle means (16.1, 16.3) extends into said second chamber (40.2), in that said disengaging means (18) comprise a cup body (18.1, 41) having generally cylindrical tubular walls and a perforated base and being mounted so as to slide axially and leaktightly relative to said needle means (16, 16.3), which base is provided with a radial portion by way of a flange (41) that slides leaktightly (seal 42) in said syringe body (11), so as to separate said first and said second chambers (40.1, 40.2) and so as to be axially pushed by said plunger (20), while an axial end portion of the wall of this body extends towards said retaining means (14.2) which comprise engaging members, for example fixed retaining fingers, which—before and during the injection—engage said needle means (16, 16.3) and oppose the action of said returning means (17) for retracting the needle means, such that, at the conclusion of the injection, said cup body is pushed by the plunger and disengages said retaining means from said needle means by means of its end portion and is then retracted with said needle means into the interior of the tubular syringe body.

4. Syringe according to claim 2, characterized in that it comprises elastic means (19, 43) interposed between one part (16.3) of said needle means (16, 16.3) and said cup body (18.1) so as to operate in the manner of an elastic return with a limited reaction force compared with said plunger (20) which is pushed axially against said body (18.1).

5. Syringe according to claim 1, characterized in that said disengaging means (52) comprise a cup body (52.1) having generally cylindrical tubular walls and an axially perforated base, of which body an open axial end portion extends towards said retaining means (14.2), in that said retaining means (14.2) comprise engaging members, for example fixed retaining fingers, which—before and during the injection—engage said needle means (51) and oppose the action of said return means (17) for retracting the needle, and in that—before and during the injection—said cup body is inserted so as to slide leaktightly (seal 15) by means of its tubular wall in a corresponding aperture (bush 14) in said first chamber (10.1), while the base portion (52.2) of the cup body extends into said second chamber (10.2) in opposition to said plunger (20), for example with an arrangement of teeth (52.4) in the form of a crown, through which teeth the injection fluid can freely flow towards the axially perforated base of the cup body (52.1), when said plunger (20) is pushed axially against said disengaging means, such that, at the conclusion of the injection, said cup body is pushed by the plunger and disengages said retaining means from said needle means by means of its end portion and is then retracted with said needle means into the interior of the tubular syringe body.

6. Syringe according to claim 5, characterized in that said needle means (51) comprises a perforated syringe needle (51.1), for example a commercially available perforated steel needle, one end of which is fixed in leaktight fluid communication to one end of a needle-supporting cannula (51.2), which can be made of a plastic material and is freely able to slide axially with the needle relative to said hole (13) in said needle-supporting head (12), and in that said cannula (51.2) is connected in leaktight fluid communication, at its other end, to said perforated base (52.2) in said cup body (52.1), by means of for example an elastic sleeve (53), so as to provide a leaktight fluid passage between said second chamber (10.2) and said needle (51.1).

7. Syringe according to claim 6, characterized in that said elastic sleeve (53) acts as an elastic return means with a limited reaction force against said plunger (20) which is pushed axially against said cup body (52.1).

8. Syringe according to claim 6, in which said elastic sleeve (53) is of bellows construction.

9. Syringe according to claim 6, in which said elastic sleeve is of a telescopic tubular structure, and elastic return means are connected to this telescopic structure.

10. Syringe according to claim 1, characterized in that said disengaging means (60) comprise a generally cylindrical tubular body (61), which may be of a plastic material, an axial end portion of which extends towards said retaining means (14.2), in that said retaining means (14.2) comprise engaging members, for example fixed retaining fingers, which—before and during injection—engage said needle means (51) and oppose the action of said return means (17) for retracting the needle, in that—before and during the injection—said tubular body is inserted so as to slide leaktightly (seal 15) by means of its tubular wall in a corresponding aperture (bush 14) in said first chamber (10.1), while the other axial end portion of this tubular body extends into said second chamber (10.2), in that an elastic sleeve means (62) passes axially through said tubular body, is connected leaktightly, at one end, to said other axial end portion of said tubular body (61), for example by means of a circumferential lip (62.2) on the edge of this end, and at the other end is connected leaktightly to said needle means (63.1, 63.2, 63.3), so as to provide a leaktight fluid passage between said second chamber (10.2) and said needle means, and in that on said sleeve means (62) is an arrangement of projections pointing towards said plunger (20), for example an arrangement of teeth (62.3) in the form of a crown, through which teeth the injectable fluid can flow freely towards said fluid passage, when said plunger (20) is pushed axially against said disengaging means, so that at the conclusion of the injection, said tubular body is pushed by the plunger and disengages said return means from said needle means of its end portion and is then retracted with said needle means into the interior of the tubular syringe body.

11. Syringe according to claim 10, characterized in that said elastic sleeve (62) acts as an elastic return means with a limited reaction force against said plunger (20) which is pushed axially against said disengaging means.

12. Syringe according to claim 10, in which said elastic sleeve (63) is of bellows construction.

13. Syringe according to claim 1, in which said needle means is formed as a single plastic part.

14. Syringe according to claim 1, characterized in that it comprises a cap (30) that contains two axial cavities (31, 32) separated from each other by an intermediate septum (33), one of which axial cavities (31) has a conical base, so that said cap (30) can assume two different positions on said syringe (10) head (12), as follows: a first position in which said cap (30) protects the tip (16.1) of the needle means by accommodating it in its cavity with the conical base (31);

and another position, rotated 180° relative to the first, in which the tip (16.1) of the needle means (16) is driven through the septum (33) of said cap and said cavity (31) with the conical base, into which said tip projects, serves as a funnel means to facilitate the measuring of fluids to be injected or mixed.

15. Syringe according to claim 1, characterized in that the tubular body (11) of the syringe comprises, at its axial end remote from the needle-supporting head (12), an integral axial jacket (70) into which a member (21.1) for actuating the plunger rod (21) passes in order to make it more difficult to prevent the automatic disarming of the needle of the syringe.

* * * * *

UNITED STATES PATENT AND TRADEMARK OFFICE
CERTIFICATE OF CORRECTION

PATENT NO.: 5,792,107

DATED: August 11, 1998

INVENTOR(S): Pasqualino PETROCELLI

It is certified that error appears in the above-identified patent and that said Letters Patent is hereby corrected as shown below:

On the cover page, item [30], "May 10, 1909" should be --May 10, 1994--.

Col. 10, claim 2, line 64, "leak tightly" should be --leaktightly--.

Signed and Sealed this

Fifth Day of January, 1999

Attest:

Attesting Officer

*Acting Commissioner of Patents and Trademarks*